US011162062B2

(12) United States Patent
Brau et al.

(10) Patent No.: US 11,162,062 B2
(45) Date of Patent: *Nov. 2, 2021

(54) METHODS AND APPARATUS FOR GAS STREAM MASS TRANSFER WITH A LIQUID

(71) Applicant: Life Technologies Corporation, Carlsbad, CA (US)

(72) Inventors: Christopher D. Brau, Logan, UT (US); Nephi D. Jones, Newton, UT (US); Benjamin R. Madsen, Nibley, UT (US); Michael E. Goodwin, Logan, UT (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/715,087

(22) Filed: Dec. 16, 2019

(65) Prior Publication Data

US 2020/0231922 A1 Jul. 23, 2020

Related U.S. Application Data

(60) Continuation of application No. 15/916,635, filed on Mar. 9, 2018, now Pat. No. 10,519,413, which is a
(Continued)

(51) Int. Cl.
*C12N 1/00* (2006.01)
*C12M 1/00* (2006.01)
(Continued)

(52) U.S. Cl.
CPC .......... *C12M 29/06* (2013.01); *B01F 3/0446* (2013.01); *B01F 3/04439* (2013.01);
(Continued)

(58) Field of Classification Search
CPC ...................................................... C12N 1/00
See application file for complete search history.

(56) References Cited

U.S. PATENT DOCUMENTS

| 3,398,935 A | 8/1968 | Livesey et al. |
| 4,510,249 A | 4/1985 | Redikultsev |
| | (Continued) | |

FOREIGN PATENT DOCUMENTS

| EP | 1 120 460 A1 | 8/2001 |
| EP | 1 837 640 A1 | 9/2007 |
| | (Continued) | |

OTHER PUBLICATIONS

Singh, "Disposable bioreactor for cell culture using wave-induced agitation," Cytotechnology 30:149-158, 1999.*
(Continued)

*Primary Examiner* — Rosanne Kosson
(74) *Attorney, Agent, or Firm* — Workman Nydegger

(57) ABSTRACT

A system for performing a gas-liquid mass transfer includes a container bounding a compartment and having a top wall, a bottom wall, and an encircling sidewall extending therebetween. A tube has a first end and an opposing second end, the first end of the tube being disposed within the compartment of the container. A nozzle is disposed within the compartment of the container and has at least one outlet, the nozzle being coupled with the tube so that a gas can be passed through the tube and out the at least one outlet of the nozzle. The nozzle is sufficiently buoyant so that when a fluid is disposed within the compartment of the container, the nozzle floats on the fluid.

20 Claims, 9 Drawing Sheets

Related U.S. Application Data division of application No. 15/187,258, filed on Jun. 20, 2016, now Pat. No. 9,932,553, which is a division of application No. 14/395,728, filed as application No. PCT/US2013/032528 on Mar. 15, 2013, now Pat. No. 9,388,375.

(60) Provisional application No. 61/625,794, filed on Apr. 18, 2012.

(51) Int. Cl.

| | | |
|---|---|---|
| *B01F 13/02* | (2006.01) | |
| *B01F 3/04* | (2006.01) | |
| *C12M 1/02* | (2006.01) | |
| *C12M 1/34* | (2006.01) | |
| *B01F 7/22* | (2006.01) | |
| *B01F 15/00* | (2006.01) | |
| *C12M 1/06* | (2006.01) | |
| *B01F 11/00* | (2006.01) | |

(52) U.S. Cl.
CPC ............ *B01F 3/04531* (2013.01); *B01F 7/22* (2013.01); *B01F 13/0205* (2013.01); *B01F 13/0211* (2013.01); *B01F 13/0272* (2013.01); *B01F 15/0085* (2013.01); *C12M 23/00* (2013.01); *C12M 23/14* (2013.01); *C12M 23/26* (2013.01); *C12M 27/00* (2013.01); *C12M 27/02* (2013.01); *C12M 29/14* (2013.01); *C12M 41/34* (2013.01); *B01F 11/0002* (2013.01); *B01F 11/0082* (2013.01); *B01F 2003/04879* (2013.01); *B01F 2003/04943* (2013.01); *B01F 2215/0073* (2013.01)

(56) References Cited

U.S. PATENT DOCUMENTS

| | | | |
|---|---|---|---|
| 4,664,526 | A | 5/1987 | Scheffler et al. |
| 5,362,147 | A | 11/1994 | Schels et al. |
| 6,655,655 | B1 | 12/2003 | Matkovich et al. |
| 7,487,688 | B2 | 2/2009 | Goodwin |
| 7,682,067 | B2 | 3/2010 | West et al. |
| 7,832,922 | B2 | 11/2010 | Schoeb |
| 7,879,599 | B2 | 2/2011 | Goodwin et al. |
| 7,992,846 | B2 | 8/2011 | Terentiev et al. |
| 8,455,242 | B2 | 6/2013 | Staheli et al. |
| 8,603,805 | B2 | 12/2013 | Goodwin et al. |
| 8,641,314 | B2 | 2/2014 | Thacker et al. |
| 2002/0131654 | A1 | 9/2002 | Smith et al. |
| 2006/0240546 | A1 | 10/2006 | Goodwin et al. |
| 2006/0270036 | A1 | 11/2006 | Goodwin et al. |
| 2011/0053228 | A1 | 3/2011 | Menon et al. |
| 2011/0207218 | A1 | 8/2011 | Staheli et al. |
| 2011/0310696 | A1 | 12/2011 | Goodwin et al. |
| 2013/0101982 | A1 | 4/2013 | Goodwin et al. |

FOREIGN PATENT DOCUMENTS

| | | |
|---|---|---|
| WO | 85/03571 | 8/1985 |
| WO | 92/05245 | 4/1992 |
| WO | 2004/061411 A2 | 7/2004 |
| WO | 2008/135991 A2 | 11/2008 |
| WO | 2013/151733 A1 | 10/2013 |

OTHER PUBLICATIONS

International Search Report and Written Opinion dated Jun. 24, 2013, issued in PCT Application No. PCT/US2013/032528, filed Mar. 15, 2013.
Chinese Office Action dated Sep. 23, 2016, issued in Chinese Application No. 201380031929.4, filed Dec. 17, 2014.
Jian Cao et al., *Food Enzymology*, ISBN 978-7-5645-0305-5, dated Feb. 28, 2011, 5 pages.
Database WPI Week 199218 Thomson Scientific, London, GB; AN 1992-150480, XP002698742.
EP19198996.1, Extended Search Report, dated Dec. 19, 2019, 6 paages.
U.S. Appl. No. 14/395,728, filed Oct. 20, 2014.
U.S. Appl. No. 15/187,258, filed Jun. 20, 2016.
U.S. Appl. No. 15/916,635, filed Mar. 9, 2018.

\* cited by examiner

METHODS AND APPARATUS FOR GAS STREAM MASS TRANSFER WITH A LIQUID

CROSS-REFERENCE TO RELATED APPLICATIONS

This application is a continuation of U.S. application Ser. No. 15/916,635, filed Mar. 9, 2018, which is a divisional of U.S. application Ser. No. 15/187,258, filed Jun. 20, 2016, now U.S. Pat. No. 9,932,553, which is a divisional of U.S. application Ser. No. 14/395,728, filed Oct. 20, 2014, now U.S. Pat. No. 9,388,375, which is a US Nationalization of PCT/US2013/032528, filed Mar. 15, 2013, which claims priority to U.S. Provisional Application No. 61/625,794, filed Apr. 18, 2012, which applications are incorporated herein by specific reference.

BACKGROUND OF THE INVENTION

1. The Field of the Invention

The present invention relates to methods and systems for producing a gas-liquid mass transfer which, in one example, can be used for oxygenating biological cultures having a shallow depth within a reactor.

2. The Relevant Technology

The growth of biological cells within a bioreactor requires critical control over a number of different process parameters. For example, as cells grow, they absorb oxygen from the surrounding media and release $CO_2$. The concentration of oxygen and $CO_2$ within the media must be carefully monitored and regulated to ensure viability and optimal growth of the cells. Another factor that needs to be carefully monitored and controlled is the density of the cells within the culture. To make sure that all of the processing parameters are properly controlled, cells are typically grown in sequential stages of increasingly larger reactors. For example, cell cultures may initially start in a small flask. Once the cell density approaches a critical value, the culture is transferred to a larger bench top reactor where the culture is combined with additional media. In turn, once the cell density again reaches a critical value, the culture is again moved to a larger reactor with more media. This process continues until a desired volume of culture is achieved. Because each different sized reactor only processes the culture over a relatively narrow change in volume, conventional techniques can be used for controlling all of the process parameters.

Although the above method of production works, there are a number of disadvantages in having to transfer the cell culture to different containers during the growth process. For example, the process is time consuming, labor intensive, and requires that the producer obtain and maintain a relatively large number of different sized reactors. In addition, the process of transferring the culture temporarily halts the preferred processing conditions, can potentially damage the cells, and increases the risk of a breach in sterility. Attempts have been made to overcome some of the above problems by trying to process a large change in volume of culture within a single reactor. For example, in contrast to conventional reactors which may only see a change in the volume of culture by a factor of two, attempts have been made to increase the change in the volume of a culture within a reactor by a factor of five.

The concept is to start with a small volume of culture within a relatively large reactor container and then through batch or continuous feed mode continue to add media to the culture as the cells grow to a point where the container reaches a predefined maximum volume of culture. Depending upon how much culture is needed, the culture can still be transferred to a larger reactor. The goal is to reduce the number of different reactors/containers the culture needs to be transferred into before reaching the desired end volume.

There are, however, a number of complications in growing a culture within a single reactor over a large change in volume. For example, in each reactor there is a mechanism for oxygenating the culture, stripping out unwanted $CO_2$, and continuously mixing the culture so that the culture remains substantially homogeneous. Mixing is commonly accomplished by an impeller disposed within the container. The impeller is sized, positioned and operated so as to achieve optimal mixing of the culture without damaging the cells. Oxygenation is typically accomplished by dispersing small diameter bubbles into the container holding the culture through a defined sparger located on the floor of the container. As the bubbles rise within the culture, the oxygen is absorbed into the culture. $CO_2$ stripping is typically accomplished by dispersing large diameter bubbles into the container through a second sparger located on the floor of the container. As the large bubbles rise within the culture, a portion of the $CO_2$ within the culture equilibrates into the air of the large bubbles and is carried out of the culture.

One of the complications of growing a culture within a single reactor over a large change in volume is that the parameters for oxygenating, stripping $CO_2$ and mixing a culture, along with other operating parameters, change as the volume of culture increases. Traditional mechanisms, as discussed above, for oxygenating, stripping $CO_2$ and mixing are designed to operate over a narrow range of fluid volumes and thus for a set configuration size do not effectively function at both small and large fluid volumes. The same is also true when other gases, such as nitrogen, are desired to be applied to the culture. Accordingly, what is needed in the art are methods and systems for oxygenating a culture and/or stripping $CO_2$ from a culture and, more generically, creating a gas-liquid mass transfer with a culture that solves all or some of the above problems and can effectively operate in conditions where traditional sparger mechanisms have difficulty performing correctly.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
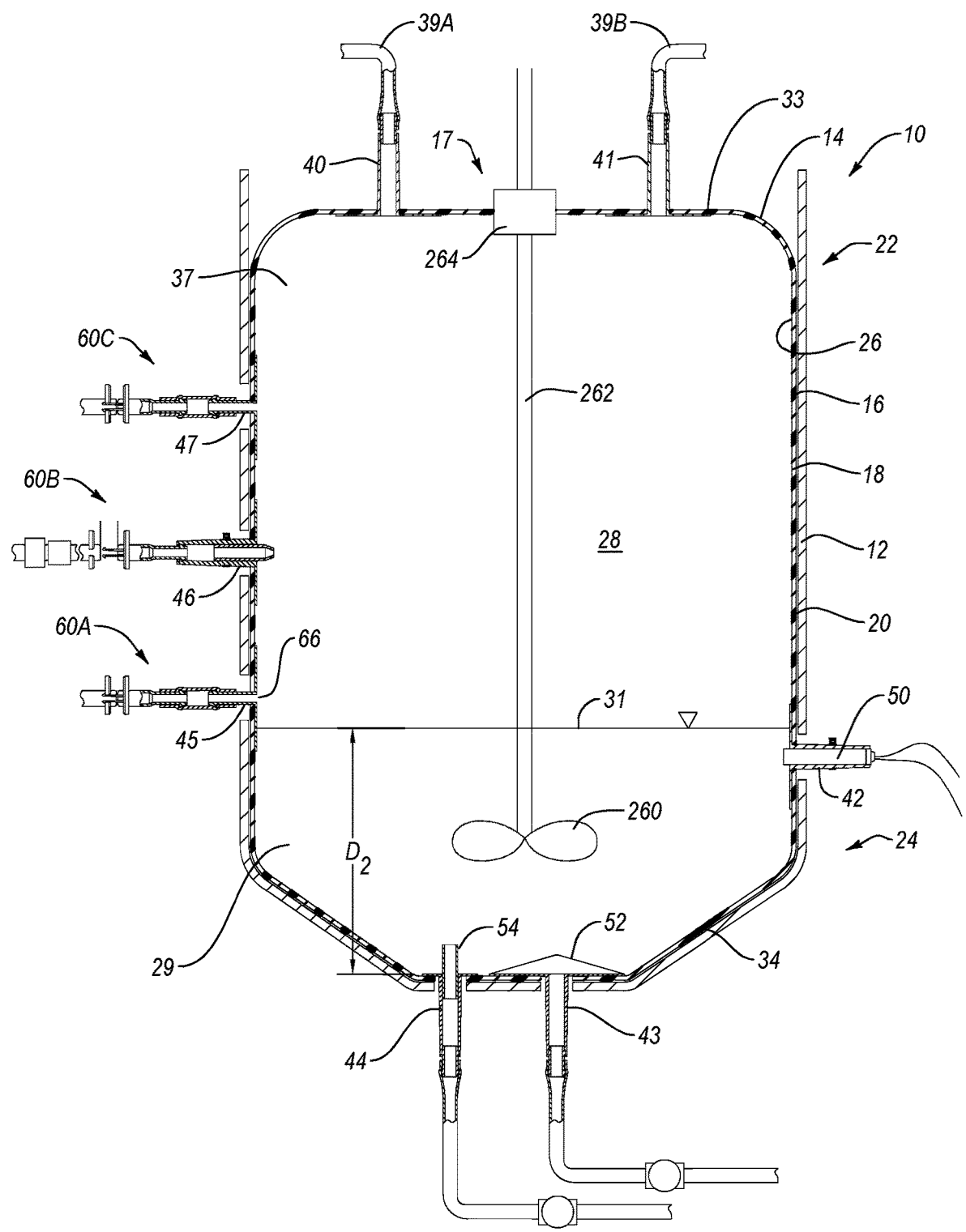
FIG. 1 is a cross sectional side view of a reactor system containing a culture.

As used in the specification and appended claims, directional terms, such as "top," "bottom," "left," "right," "up," "down," "upper," "lower," "proximal," "distal" and the like are used herein solely to indicate relative directions and are not otherwise intended to limit the scope of the invention or claims.

The present invention relates to novel methods and systems for efficiently producing a gas-liquid mass transfer and for particularly producing a gas-liquid mass transfer with shallow volumes of liquid. In one embodiment, the methods and systems can be used in oxygenating a biological culture disposed within a reactor container and particularly cultures having a relatively shallow depth. For example, the methods and systems can commonly be used in bioreactors and fermentors for culturing cells or microorganisms. Specifically, the inventive methods and systems can be used in culturing bacteria, fungi, algae, plant cells, animal cells, protozoan, nematodes, and the like. The methods and systems can also be used in association with the formation and/or treatment of solutions and/or suspensions that are for biological purposes, such as media, buffers, or reagents. For example, the methods and systems can be used in the formation of media where sparging is used to control the pH of the media through adjustment of the carbonate/bicarbonate levels with controlled gaseous levels of carbon dioxide. In other applications, the methods and systems can be used for stripping gases, such as oxygen or $CO_2$ from a culture or fluid. It is appreciated that the inventive methods and systems are not limited to being used with biological cultures but can also be used in food production, chemical production, biopharmaceutical production and other types of production where a gas-liquid mass transfer is desired.

In general, one embodiment of the inventive method comprises passing a stream of a gas over a top surface of a liquid at a sufficient velocity and direction so that the gas stream produces turbulence on the top surface of the liquid that is sufficient to produce a mass transfer between the stream of gas and the liquid. This process is referred to herein as "gas stream mass transfer" or, where the process is used for oxygenating a fluid, the process can be referred to as "gas stream oxygenation." The process is similar to how wind passing over the surface of a lake creates Langmuir circulations to oxygenate the lake water. That is, as a result of the gas stream flowing over the surface of the liquid, there is both an efficient mass transfer of the gas into the fluid and there is a vertical circulation of the fluid near the surface. This circulation of the fluid ensures that the upper layer of the fluid has a uniform gas concentration. In turn, an impeller or other mixing system can be used to ensure that the upper layer of the fluid is uniformly mixed throughout the remainder of the fluid so that the entire fluid has a proper gas concentration. In other applications, as mentioned above and as will be discussed below in greater detail, the same process of passing a gas stream over the top surface of a fluid so as to produce fluid turbulence can be used for stripping gas out of the fluid.

Although gas stream mass transfer is primarily discussed herein with regard to oxygenating a biological culture, the same methods and systems can also be used for oxygenating other types of liquids, such as those mentioned above. In addition, as discussed below in greater detail, the inventive methods and systems are not limited to oxygenating a fluid but can be used with other gases for affecting any type of mass transfer into a liquid and/or out of a liquid.

Gas stream mass transfer has a number of processing advantages when it is used for oxygenating a biological culture within a reactor container, particularly over conventional sparging techniques. Where a reactor container is being designed to process a culture of cells or microorganisms over a relatively large change in fluid volume, the diameter of the container typically needs to be relatively large to maintain geometry and height requirements. As the diameter of the container increases with respect to volume, the depth of the culture within the container decreases. As a result, for very small volumes of culture within the container, such as when the initial volume of culture is transferred into the container, the resident time for the oxygenating bubbles that are typically sparged into the culture from the floor of the container is insufficient to properly oxygenate the culture. That is, because the depth of culture is so shallow, the oxygenating bubbles are not within the culture for a sufficient period of time to fully oxygenate the culture as the bubbles travel from the sparger to the top surface of culture. Likewise, the resident time for the larger sparged bubbles used to strip out the $CO_2$ is also insufficient to fully remove the unwanted $CO_2$ from the culture. This problem is further compounded by the fact that the $CO_2$ gas is heavier than air so that the $CO_2$ lays like a blanket over the top surface of the culture, thereby further hampering oxygenation of the culture and removing $CO_2$.

In contrast to sparging which becomes more efficient as the depth of the culture increases, gas stream oxygenation or mass transfer, which is accomplished by blowing a stream of air or other gas containing oxygen over the top surface of the culture, become more efficient as the depth of the culture or other fluid being processed decreases. Thus, gas stream oxygenation is particularly useful for shallow depth cultures disposed within a reactor; including reactors that start with a small volume and increase to a large volume. In addition, sparging is known to produce unwanted foam on the top surface of cultures, especially when the spargers used generate very small bubbles (sub millimeter diameter). In contrast, gas stream mass transfer produces minimal foaming and can assist in reducing the vessel foam generation by reducing the amount of traditional sparging required. Furthermore, gas stream oxygenation prevents the formation of a $CO_2$ blanket on the surface of the culture. As such, the gas on the surface of the culture is both well controlled and well mixed, permitting the $CO_2$ to dissipate out of the culture, mix into the head space of the reactor, and leave via the system exhaust port. The interaction of the gas stream oxygenation with the system liquid also helps directly facilitate stripping $CO_2$ from the culture. Accordingly, for relatively shallow depth cultures, gas stream oxygenation can be used to both oxygenate the culture and remove $CO_2$ from the culture, in some cases eliminating the need for traditional sparging in certain forms of the invention.

As the depth of a culture within a reactor increases, the efficiency of oxygenating the culture at the bottom of the reactor through gas stream oxygenation decreases. Accordingly, as the depth of the culture increases, $dO_2$ sensors or other parameters or mechanisms can be used to determine when sparging or other methods of oxygenation should be activated. That is, as the depth of the culture increases, sparging can be activated such as through stepped increments or through continuous gradual increase so as to ensure that the culture is always properly oxygenated. The applied gas stream oxygenation can decrease as sparging increases or can remain constant. Even if the gas stream is not fully oxygenating the culture, the gas stream is still equilibrating the upper region of the culture and preventing $CO_2$ blanketing which in turn assists in traditional sparge operation. Thus, even for relatively deep volumes of culture, gas stream oxygenation can continue to be used in conjunction with sparging or other methods of oxygenation. It should be appreciated that an electronic controller could be used to automatically activate and/or regulate sparging and gas flow based on sensor readings.

Turning to the Figures, examples of systems will now be discussed that can be used in performing gas stream oxygenation/mass transfer. Depicted in FIG. 1 is one embodiment of a reactor system 10 incorporating features of the present invention. In general, reactor system 10 comprises a support housing 12 that bounds a chamber 14, a container assembly 16 disposed within chamber 14 and a mixing system 17 coupled with container assembly 16. Support housing 12 typically comprises a rigid tank, such as a metal tank. The tank can be jacketed for controlling the temperature of the culture within container assembly 16. Support housing 12 can be any desired size, shape, or configuration that will properly support container assembly 16, as discussed below.

With continued reference to FIG. 1, container assembly 16 comprises a container 18 having a side 20 that extends from an upper end 22 to an opposing lower end 24. Upper end 22 terminates at an upper end wall 33 while lower end 24 terminates at a lower end wall 34. Container 18 also has an interior surface 26 that bounds a compartment 28. Compartment 28 is configured to hold a fluid. The fluid can comprise a biological culture which comprises cells or microorganisms, media, and other nutrients and additives. Any other type of fluid can also be used that requires mass transfer with a gas. For example, the fluid can be a chemical, biological fluid, food product, or other fluid. For the example herein, the fluid will be discussed as biological culture 29. Culture 29 has a top surface 31. A head space 37 is disposed within compartment 28 and is bounded between top surface 31 of culture 29 and upper end wall 33.

In the embodiment depicted, container 18 comprises a flexible bag that is comprised of a flexible, water impermeable material such as a low-density polyethylene or other polymeric sheets or film having a thickness in a range between about 0.1 mm to about 5 mm with about 0.2 mm to about 2 mm being more common. Other thicknesses can also be used. The material can be comprised of a single ply material or can comprise two or more layers which are either sealed together or separated to form a double wall container. Where the layers are sealed together, the material can comprise a laminated or extruded material. The laminated material comprises two or more separately formed layers that are subsequently secured together by an adhesive. Examples of extruded material that can be used in the present invention include the HyQ CX3-9 and HyQ CX5-14 films available from HyClone Laboratories, Inc. out of Logan, Utah. The material can be approved for direct contact with living cells and be capable of maintaining a solution sterile. In such an embodiment, the material can also be sterilizable such as by ionizing radiation. Prior to use, container assembly 16 is typically sealed closed and sterilized so that compartment 28 is sterile prior to the introduction of culture 29.

In one embodiment, container 18 can comprise a two-dimensional pillow style bag. In another embodiment, container 18 can be formed from a continuous tubular extrusion of polymeric material that is cut to length. The ends can be seamed closed or panels can be sealed over the open ends to form a three-dimensional bag. Three-dimensional bags not only have an annular sidewall but also a two dimensional top end wall and a two dimensional bottom end wall. Three dimensional containers can comprise a plurality of discrete panels, typically three or more, and more commonly four or six. Each panel is substantially identical and comprises a portion of the sidewall, top end wall, and bottom end wall of the container. Corresponding perimeter edges of each panel are seamed together. The seams are typically formed using methods known in the art such as heat energies, RF energies, sonics, or other sealing energies.

In alternative embodiments, the panels can be formed in a variety of different patterns. Further disclosure with regard to one method of manufacturing three-dimensional bags is disclosed in US Publication No. US 2002-0131654 A1, published Sep. 19, 2002, which is incorporated herein by specific reference in its entirety.

It is appreciated that container 18 can be manufactured to have virtually any desired size, shape, and configuration. For example, container 18 can be formed having a compartment sized to 10 liters, 30 liters, 100 liters, 250 liters, 500 liters, 750 liters, 1,000 liters, 1,500 liters, 3,000 liters, 5,000 liters, 10,000 liters or other desired volumes. The size of the compartment can also be in the range between any two of the above volumes. Although container 18 can be any shape, in one embodiment container 18 is specifically configured to be generally complementary to chamber 14 of support housing 12 in which container 18 is received so that container 18 is properly supported within chamber 14.

Although in the above discussed embodiment container 18 is depicted as a flexible bag, in alternative embodiments it is appreciated that container 18 can comprise any form of collapsible container or semi-rigid container. In still other embodiments, container 18 can be rigid and support housing 12 can be eliminated.

Continuing with FIG. 1, formed on container 18 are examples of a plurality of different ports that can be mounted thereon with each of the ports communicating with compartment 28. Specifically, mounted on upper end wall 33 are access ports 40 and 41 having lines 39A and B coupled therewith, respectively. Access ports 40 and 41 can be used for delivering gas, media, cultures, nutrients, and/or other components into container 18 and can be used for withdrawing culture 29 or gas from within head space 37. For example, in some forms of the invention, port 40 can be used as a gas inlet into head space 37 and port 41 can be used as a gas outlet from head space 37. Any desired number of access ports can be formed on container 18. A sensor port 42 is formed on side 20 of container 18. A sensor 50 is disposed within sensor port 42 so as to communicate with compartment 28, typically at the lower end thereof. It is appreciated that any number of sensor ports 42 can be formed on container 18 each having a corresponding sensor 50 disposed therein. Examples of sensors 50 that can be used include temperatures probes, pH probes, dissolved oxygen sensors, carbon dioxide sensors, cell mass sensors, nutrient sensors, and any other sensors that allow for testing or checking the culture or production. The sensors can also be in the form of optical sensors and other types of sensors.

Mounted on lower end wall 34 are sparging ports 43 and 44. A first sparger 52 is mounted to port 43 and is designed to deliver small bubbles to culture 29 for oxygenating culture 29. Sparger 52 can be formed integral with or attached to port 43. A second sparger 54 is mounted to port 44 and is designed to deliver larger bubbles to culture 29 for stripping $CO_2$ from culture 29. As such, the bubbles from first sparger 52 are smaller than the bubbles from second sparger 54. In some forms of the invention, second sparger 54 can be an open tube or a tube with a porous frit with relatively large pores, while first sparger 52 can be a tube with a porous frit with relatively small pores. First sparger 52 can also comprise a perforated or porous membrane that is mounted on the end of port 43 or on the interior surface of lower end wall 34 so as to extend over port 43. It is appreciated that spargers come in a variety of different configurations and that any type of spargers can be used as desired or as appropriate for the expected culture volumes, cells and conditions.

It is again noted that container 18 can be formed with any desired number of ports and that the ports can be formed at any desired location on container 18. The ports can be the same configuration or different configurations and can be used for a variety of different purposes such as listed above but not limited thereto. Examples of ports and how various probes, sensors, and lines can be coupled thereto is disclosed in US Publication No. 2006-0270036, published Nov. 30, 2006 and US Publication No. 2006-0240546, published Oct. 26, 2006, which are incorporated herein by specific reference in their entirety. The ports can also be used for coupling container 18 to secondary containers, to condenser systems, and to other desired fittings.

Figure 2:
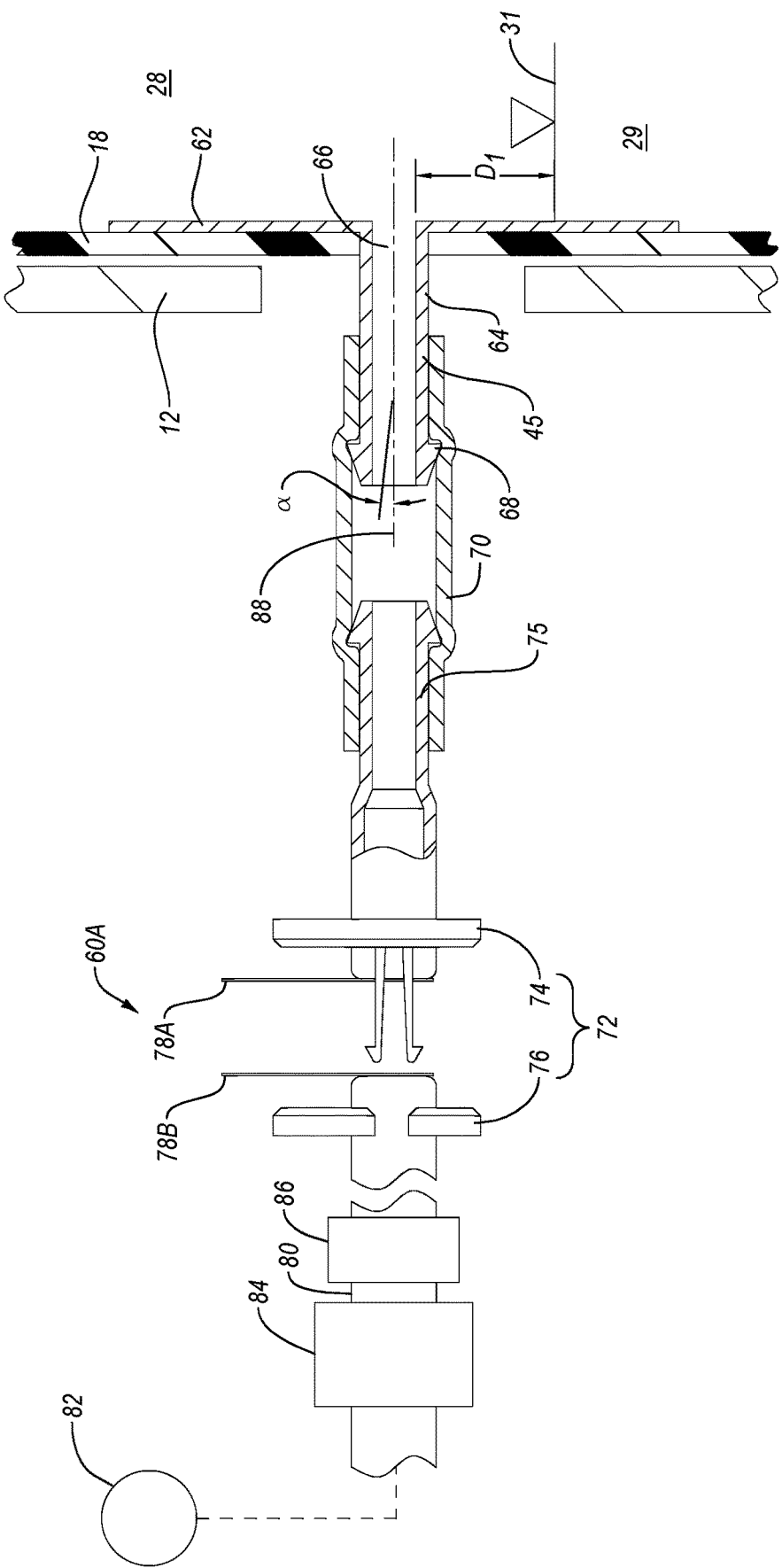
FIG. 2 is a partial cross sectional side view of one embodiment of a gas delivery system shown in FIG. 1.

Also disposed along side 20 of container 18 are a plurality of vertically spaced apart gas ports 45-47. Each of ports 45-47 forms part of a corresponding gas delivery system, which systems are designed for delivering gas into compartment 28 to produce gas stream oxygenation/mass transfer. Depicted in FIG. 2 is an enlarged view of a gas delivery system 60A which includes gas port 45. Port 45 comprises a flange 62 mounted to container 18 and a tubular stem 64 outwardly projecting therefrom. Stem 64 bounds a passageway 66 longitudinally extending therethrough so as to communicate with compartment 28. An annular barb 68 is formed on the free end of stem 64 and couples with a tube 70. In turn, tube 70 couples with an aseptic connector 72.

Aseptic connector 72 includes a first connector portion 74 that selectively mates with and fluid couples to a second connector portion 76. A tubular stem 75 projects from first connector portion 74 and fluid couples with tube 70. Each of connector portions 74 and 76 have a sealing layer 78A and B, respectively, that covers the opening to connector portions 74 and 76. After connector portions 74 and 76 are coupled together, sealing layers 78A and B are pulled out from between the connector portions so as to form an aseptic fluid connection between connector portions 74 and 76. Aseptic connectors are known in the art. One example of an aseptic connector is the KLEENPACK® connector produced by the Pall Corporation. The PALL connector is described in detail in U.S. Pat. No. 6,655,655, the content of which is incorporated herein by reference in its entirety. Other aseptic connectors can also be used.

A tube 80 fluid couples with second connector portion 76 and extends to a gas supply 82. Gas supply 82 delivers a gas which passes through aseptic connector 72, port 45 into compartment 28. The gas can be oxygen or it can be a gas containing oxygen, such as air. Other gases can also be used depending on the desired application. Gas supply 82 can comprise a pressurized canister, a compressor, or other gas supply source. Disposed along tube 80 is a gas filter 84 that sterilizes the gas as it passes therethrough. Also mounted along tube 80 is a valve 86. Valve 86 is used to selectively stop the flow of gas through delivery system 60A and to prevent culture 29 within container 18 from flowing out through delivery system 60. Valve 86 can have a variety of different configurations. For example, valve 86 can comprise a ball valve, a gate valve, a clamp that pinches tube 80 or any other type of valve that functions for the intended purpose. Valve 86 can be manually controlled or can be electric, hydraulic, pneumatic or the like. It is appreciated that valve 86 can be positioned anywhere along delivery system 60 but is typically located close to gas port 45. In one embodiment, valve 86 can be mounted on tube 70 adjacent to port 45 or directly on port 45.

As previously discussed, the object of gas delivery system 60 is to deliver a stream of gas over top surface 31 of culture 29 or other applicable fluid at a sufficient velocity and direction so that the gas stream produces a turbulence on top surface 31 that is sufficient to oxygenate the culture for growing the cells or microorganisms therein. The term "over" is broadly intended to include the gas traveling over top surface 31 in any desired orientation such as horizontal, substantially horizontal, downwardly inclined, or upwardly inclined. The gas stream need not flow in a linear path but can flow in a circular path or vortex, such as about a vertical or horizontal axis, or can flow along a random path. The gas stream can be a laminar flow or a turbulent flow and the direction, flow rate, and/or speed of the gas flow can be constant or variable. For example, the gas stream can change from a downward vertical direction to a substantially horizontal direction. By placing gas port 64 on side 20 of container 18, the gas passing out through passageway 66 in this embodiment travels horizontally or substantially horizontally within compartment 28 so that it can pass over and across top surface 31. In some embodiments, the gas stream oxygenation can be sufficient to independently oxygenate the culture to the extent needed for growing the cells or microorganisms without any other form of oxygenation, such as sparging. In other embodiments, the gas steam oxygenation can be used in conjunction with sparging or other oxygenation processes.

In one embodiment, the gas stream oxygenation is able to achieve a mass transfer of oxygen using only air and without the aid of sparging having a kLa factor that is greater than 3 and more commonly greater than 5 or 7. The gas stream oxygenation can also maintain, without separate sparging, a stable oxygen concentration set point within the active culture that is in a range of 30%-50% of air saturation. The above values can be achieved in a stirred tank reactor with mixing by impeller and in other types of rectors. In one specific example, gas stream oxygenation, using only air, was able to oxygenate a CHO culture at a target value of 50% of air saturation (868 mbar ambient pressure) and strip $CO_2$ to a cell concentration of 3.5E+06 cell/mL at $\frac{1}{5}^{th}$ vessel volume. At this point the culture was then fed media to full vessel volume. It is worth noting that the oxygenation and $CO_2$ stripping provided by the gas stream oxygenation was excessive at this level of culture density and vessel fill volume; it required the addition of $N_2$ and $CO_2$ mixed in with the air to hold target pH and dissolved $O_2$ target values.

During operation, compartment 28 of container 18 is filled with culture 29 so that top surface 31 is disposed close to passageway 66. In one embodiment, the distance $D_1$ between passageway 66 and top surface 31 is in a range between about 0.75 cm to about 15 cm with about 1 cm to about 10 cm or about 2 cm to about 5 cm being more common. Other distances can also be used. Furthermore, the distance $D_1$ can vary based upon factors such as the size of container 18, the projection angle of the gas (with flow perpendicular to the liquid surface being optimal), the flow rate of the gas, and the superficial velocity of the gas. When measuring the distance $D_1$, top surface 31 can be the maximum liquid wave height under agitation of culture 29 or can be top surface 31 with no agitation. For scalable representation, the flow rate can be measured in rate of Vessel Volumes per Minute (VVM) of the maximum rated liquid working volume of the system. The flow rate of the gas passing out through passageway 66 is typically in a range between about 0.06 VVM to about 0.2 VVM with about 0.08 VVM to about 0.1 VVM or about 0.16 VVM to about 0.18 VVM being more common. Other flow rates can also be used depending on the intended application. The velocity of the gas exiting passageway 66 or traveling across top surface 31 within compartment 28 is typically in a range between about 25 m/sec to about 275 m/sec with about 25 m/sec to about 175 m/sec or about 30 m/sec to about 100 m/sec being more common. The velocity can be greater than 25 m/sec and more commonly greater than 40 m/sec, 60 m/sec, 80 m/sec, or 100 m/sec. To achieve desired gas velocities exiting passageway 66, passageway 66 can have a minimum exit area of flux based on the volume of compartment 12, i.e., vessel volume (VV). This minimum exit area of flux can be in a range between about VV (liters)/80 (liters/mm$^2$) to about VV (liters)/7.8 (liters/mm$^2$) with about VV (liters)/40 (liters/mm$^2$) to about VV (liters)/30 (liters/mm$^2$) or about VV (liters)/8.5 (liters/mm$^2$) to about VV (liters)/6.25 (liters/mm$^2$) being more common. Other areas can also be used.

If desired, port 45 can be configured so that during operation stem 64 is angled so that the gas passing out therethrough is directed slightly down towards top surface 31. For example, stem 64 has a central longitudinal axis 88. Port 45 can be formed so that axis 88 of stem 64 is tilted relative to horizontal during use by an angle at in a range between 1° to about 10° so that the gas passing out therethrough passes slightly down against top surface 31. Other angles can also be used.

As previously discussed, gas stream oxygenation is most efficient for shallow depths of culture 29 within container 18. In one embodiment, the maximum distance $D_2$ (FIG. 1) between top surface 31 and lower end wall 34 at which the gas stream oxygenation can independently oxygenate culture 29 to grow cells or microorganisms can be in a range of distances based on diameter of the container 18, i.e., vessel diameter (VD). For example, maximum distance $D_2$ can be in a range between about VD (cm)*0.3 to about VD (cm)*0.4. Where container 18 does not have a circular transverse cross section, VD can be based on an average diameter. In some specific examples, $D_2$ can be in a range between about 5 cm to 30 cm or between 10 cm and 100 cm depending on the diameter of the container. Other distances can also be used. At some depths, the system can operate without the use of sparging or other oxygenation systems. In addition, for some depths desired oxygenation can be achieved through-out the culture without the use of a separate mixer due to the natural circulation caused by the blowing gas. As the depth increases, however, proper oxygenation of the culture requires both gas steam oxygenation and a separate mixing system, such as thorough an impeller or rocking, to ensure all of the culture is properly oxygenated.

As the depth of culture 29 increases, sensors 50 may detect the need for additional oxygenation, even when mixing is being accomplished. An electrical controller or manual regulator can then be used to regulate the flow of sparged gas through spargers 52 and 54 for further controlling the oxygenation and $CO_2$ levels within culture 29. Although sparging with air or oxygen may not be required at shallow depths when using gas steam oxygenation, sparging with nitrogen, such as through sparger 54, may still be used at all depths to control the oxygen within the culture, i.e., to strip out excess oxygen produced by gas steam oxygenation. Although gas delivery system 60A is shown in FIG. 1 as the only gas delivery system that is located at or near the elevation on container 18 corresponding to the top of distance $D_2$, two or more gas delivery systems 60A can be located and simultaneously operated at or near that same elevation.

The gas delivered to container 18 through gas delivery system 60A can be drawn out through access port 41 so that container 18 does not over inflate. Because of the rather high volume of gas passing through container 18, there can be a higher rate of evaporation of the media relative to conventional systems. As such, reactor system 10 can be operated with a condenser that couples with access port 41. One example of a condenser that can be used with reactor system 10 is disclosed in US Publication No. 2011/0207218 A1, published Aug. 25, 2011, which is incorporated herein by specific reference in its entirety.

Culture 29 continues to grow at a level below passage 66 until a defined mass density or other desired value is determined within culture 29. Valve 86 can then be closed and media and other components added to culture 29 until the level of top surface 31 is raised to within an operating distance from a second gas delivery system 60B shown in FIG. 1. Gas delivery system 60B is then activated to again pass a gas stream over top surface 31 and thereby continue with the gas stream oxygenation of culture 29. This process can then be continued for a subsequent gas delivery system 60C. Likewise, any number of additional gas delivery systems can be vertically spaced apart along side 20 of container 18 for continuing gas stream oxygenation at other elevations.

Figure 7:
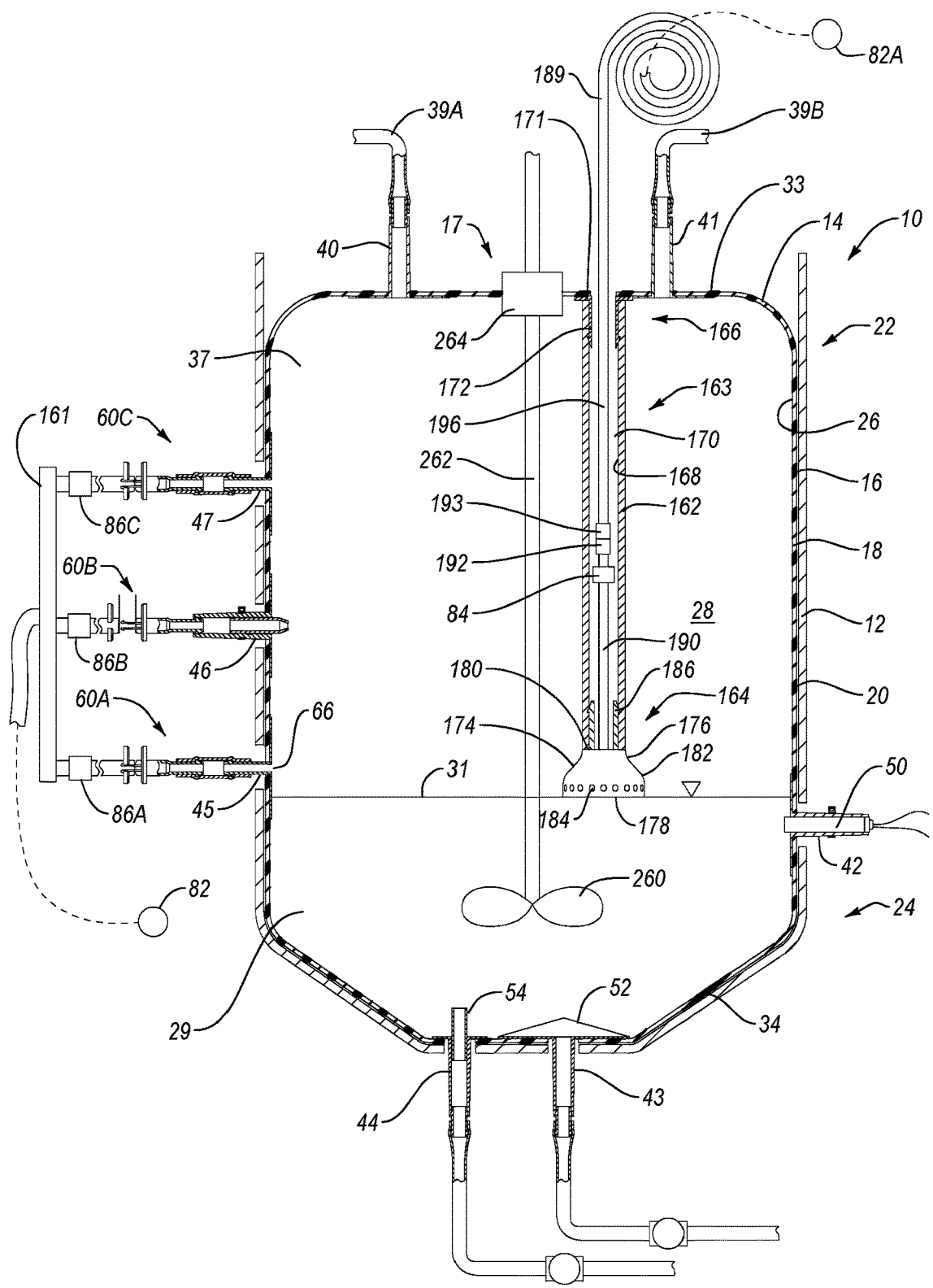
FIG. 7 is a cross sectional side view of the reactor system shown in FIG. 1 including a further alternative embodiment of a gas delivery system that adjustably extends down from the upper end wall of the container.

In one embodiment, each of gas delivery systems 60A-C can be coupled to a separate gas supply 82 (FIG. 2). In an alternative embodiment, however, as depicted in FIG. 7, a manifold 161 can be fluid coupled to each gas delivery system 60A-C while a single gas supply 82 is coupled with manifold 161. Valves 86A-C incorporated into gas delivery systems 60A-C, respectively, can be opened and closed by a common controller to regulate which gas delivery system 60A-C is opened for gas to travel therethrough.

Figure 3:
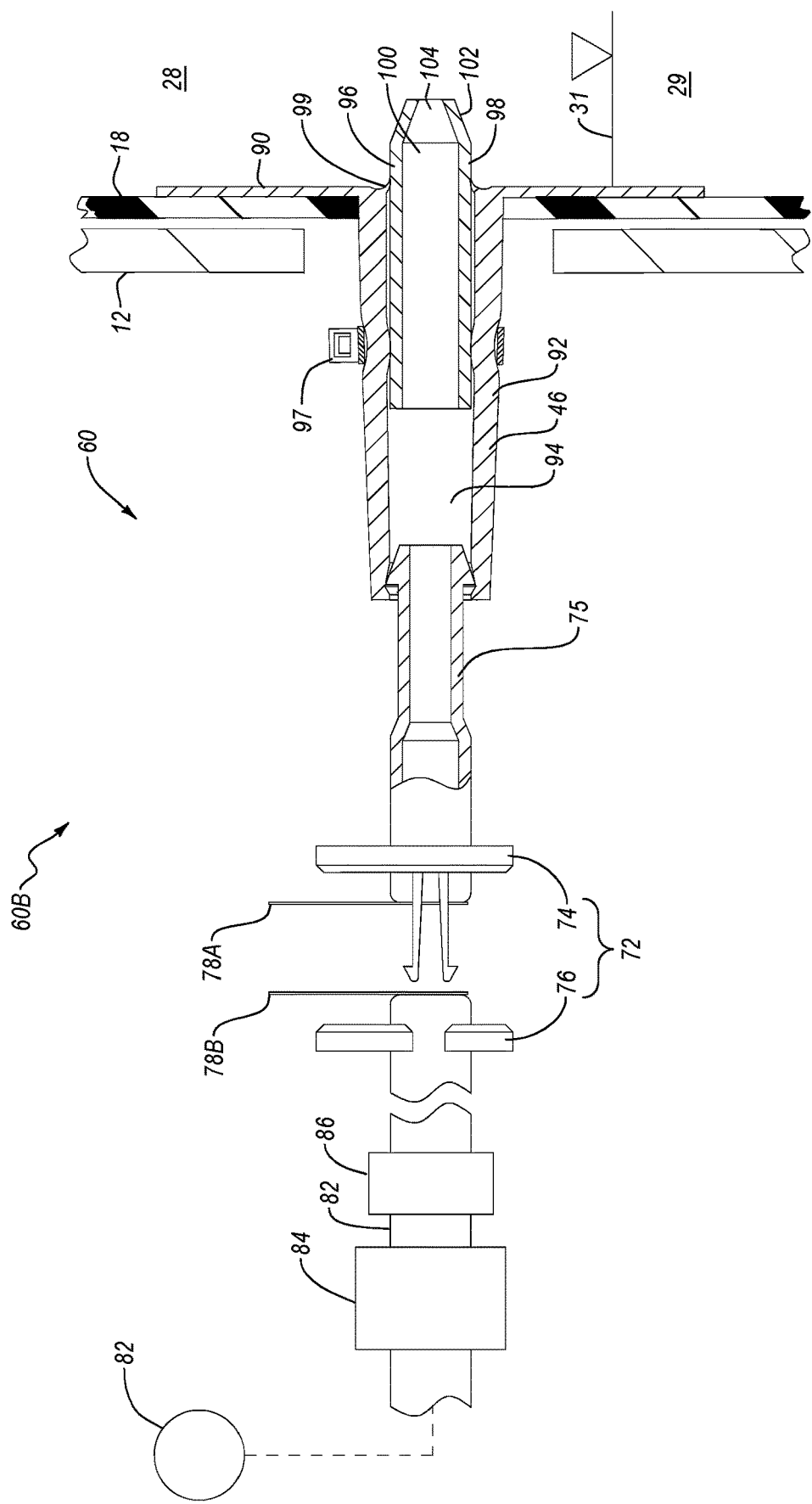
FIG. 3 is a partial cross sectional side view of an alternative embodiment of a gas delivery system shown in FIG. 1.

It is appreciated that each of gas delivery systems 60A-C can have the same configuration as gas delivery system 60A. In alternative embodiments, gas delivery systems 60A-C can have a different configuration or the gas delivery systems can be different from each other. For example, depicted in FIG. 3 is an enlarged view of a gas delivery system 60B. Like elements between gas delivery systems 60A and 60B are identified by like reference characters. In contrast to gas delivery system 60A which uses port 45 having a rigid barbed stem 64, gas delivery system 60B uses gas port 46 having a flange 90 secured to container 18 and a tubular stem 92 outwardly projecting therefrom. Flange 90 and stem 92 are comprised of a resiliently flexible material typically having a durometer on a Shore A scale with a value of less than 90. Further disclosure with regard to port 46 is disclosed in US Publication No. 2006-0240546, which was previously incorporated herein by specific reference.

Stem 92 bounds a passageway 94 that communicates with compartment 28. Disposed within passageway 94 is a nozzle 96 that is secured to stem 92 by a pull tie 97 or other type of clamp. An annular lip seal 99 inwardly projecting from stem 92 can from a liquid tight seal about nozzle 96. Nozzle 96 is tubular having an encircling sidewall 98 that bounds a passageway 100 extending therethrough. Nozzle 96 has a tip 102 which bounds an outlet 104 through which the gas passes from passageway 100 into compartment 28. Nozzle 96 is configured so that outlet 104 has the desired size and configuration to achieve the desired gas velocity and flow rate to achieve gas stream oxygenation. The distances, dimensions, velocities, flow rates, orientations and the like discussed above with regard to gas delivery system 60A and passageway 66 are also applicable to gas delivery system 60B and passageway 100/outlet 104. Although nozzle 96 is shown having a single outlet 104 formed thereon, in alternative embodiments, nozzle 96 can be formed with a plurality of radially spaced apart outlets 104 so that the gas stream fans out across more of the surface of top surface 31. As a result of using nozzle 96, a standardized port 46 can be used on container 18 while a specifically designed nozzle 96 can be used for achieving the desired gas flow conditions.

Figure 4:
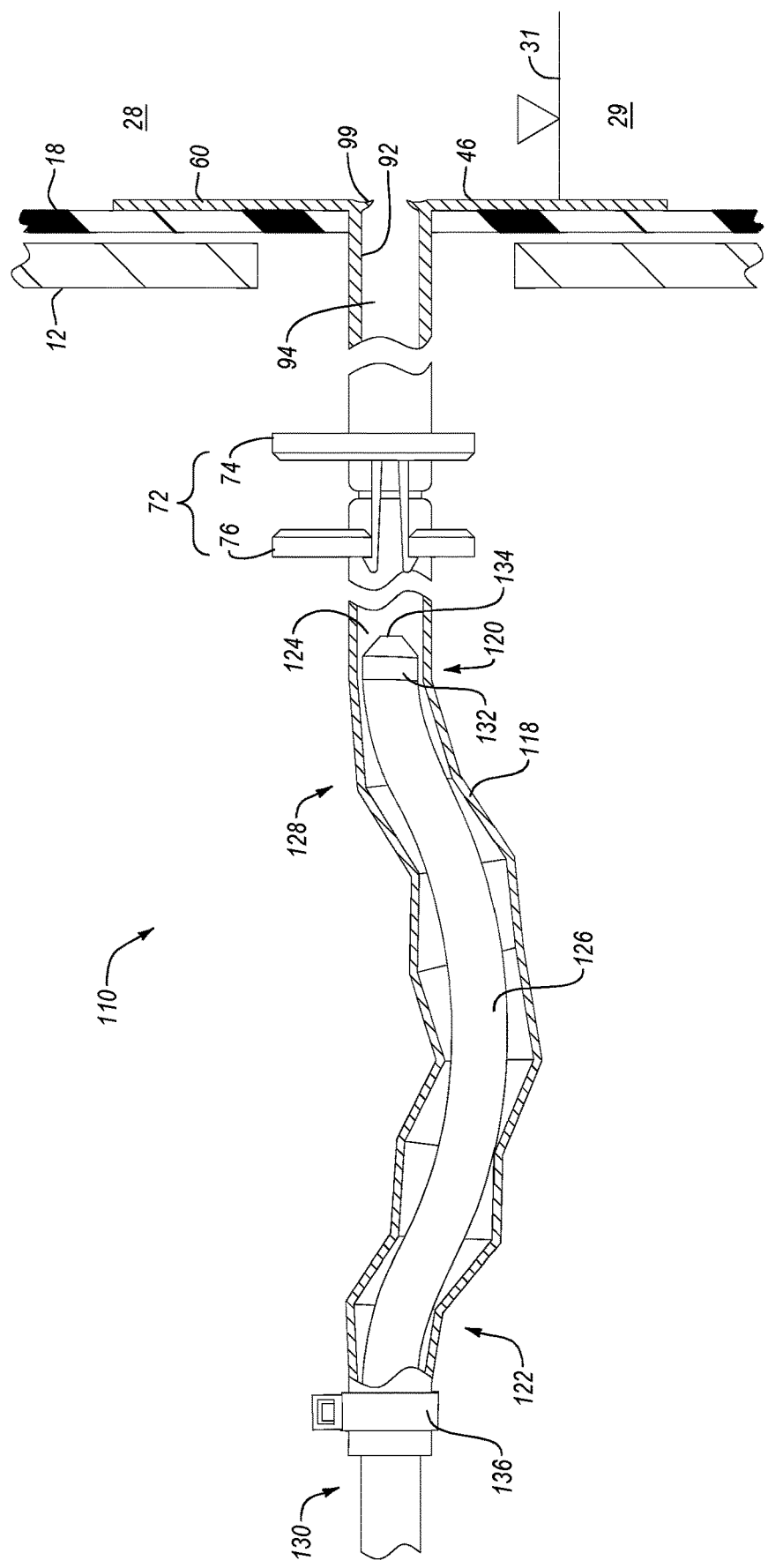
FIG. 4 is a partial cross sectional side view of another alternative embodiment of a gas delivery system in a first position that can be used with the reactor shown in FIG. 1.

Depicted in FIG. 4 is another alternative embodiment of a gas delivery system 110 for delivering a gas stream to compartment 28 of container 18. Again, like elements with prior embodiments are identified by like reference characters. Gas delivery system 110 comprises port 46 having flange 60 coupled to container 18 and tubular stem 92 outwardly projecting therefrom. Fluid coupled to the end of stem 92 is first connector portion 74 of aseptic connector 72 which can be selectively coupled with second connector portion 76. Coupled with the upstream side of second connector portion 76 is a tubular sleeve 118. Tubular sleeve 118 has a first end 120 coupled with second connector portion 76 and an opposing second end 122. Sleeve 118 is comprised of a flexible material that can be easily collapsed, such as by folding, gathering, compressing or the like, along its length. For example, sleeve 118 can be comprised of a polymeric sheet or film. As such, tubular sleeve 118 can be in the form of a flexible bag having openings at opposing ends. In an alternative embodiment, sleeve 118 can comprise a molded tube wherein the encircling wall is accordioned for easy collapsing and expansion. Other configurations can also be used so that sleeve 118 folds, gathers, or compresses as second end 122 is pushed towards first end 120.

Tubular sleeve 118 bounds a chamber 124. Disposed within chamber 124 is an end portion of a flexible tube 126. Tube 126 has a first end 128 disposed within chamber 124 and an opposing second end 130. Disposed on first end 128 of tube 126 is a nozzle 132 having an outlet 134 formed thereon. A clamp 136 encircles sleeve 118 at second end 122 and compresses against the exterior surface of tube 126 so as to secure sleeve 118 and tube 126 together and form a liquid tight seal therebetween. As will be discussed below in greater detail, the portion of tube 126 within sleeve 118 can be formed having a resilient curved arch along the length thereof. Second end 130 of tube 126 either directly or indirectly couples with gas supply 82 and can have gas filter 84 and valve 86 disposed there along (FIG. 2).

During operation, gas delivery system 110 can be operated in a number of different positions. For example, once connector portions 74 and 76 are coupled together and sealing layers 78 removed, an opening is formed through aseptic connector 72 that communicates with chamber 124 of sleeve 118. In this configuration, second end 122 of sleeve 118 can be manually pushed towards first end 122. Because tube 126 is secured to sleeve 118 by clamp 136, the advancing of second end 122 causes first end 128 of tube 126 to concurrently advance through aseptic connector 72 and into or through passageway 94 of port 46. Where top surface 31 of culture 29 is disposed adjacently below passageway 94 of port 46, nozzle 132 can remain disposed with passageway 94 or can extend slightly into chamber 28 for blowing gas across top surface 31 in substantially the manner as discussed above with regard to nozzle 96. This configuration has the advantage that lip seal 99 can seal against tube 126 to prevent any fluid from passing into port 46.

Figure 5:
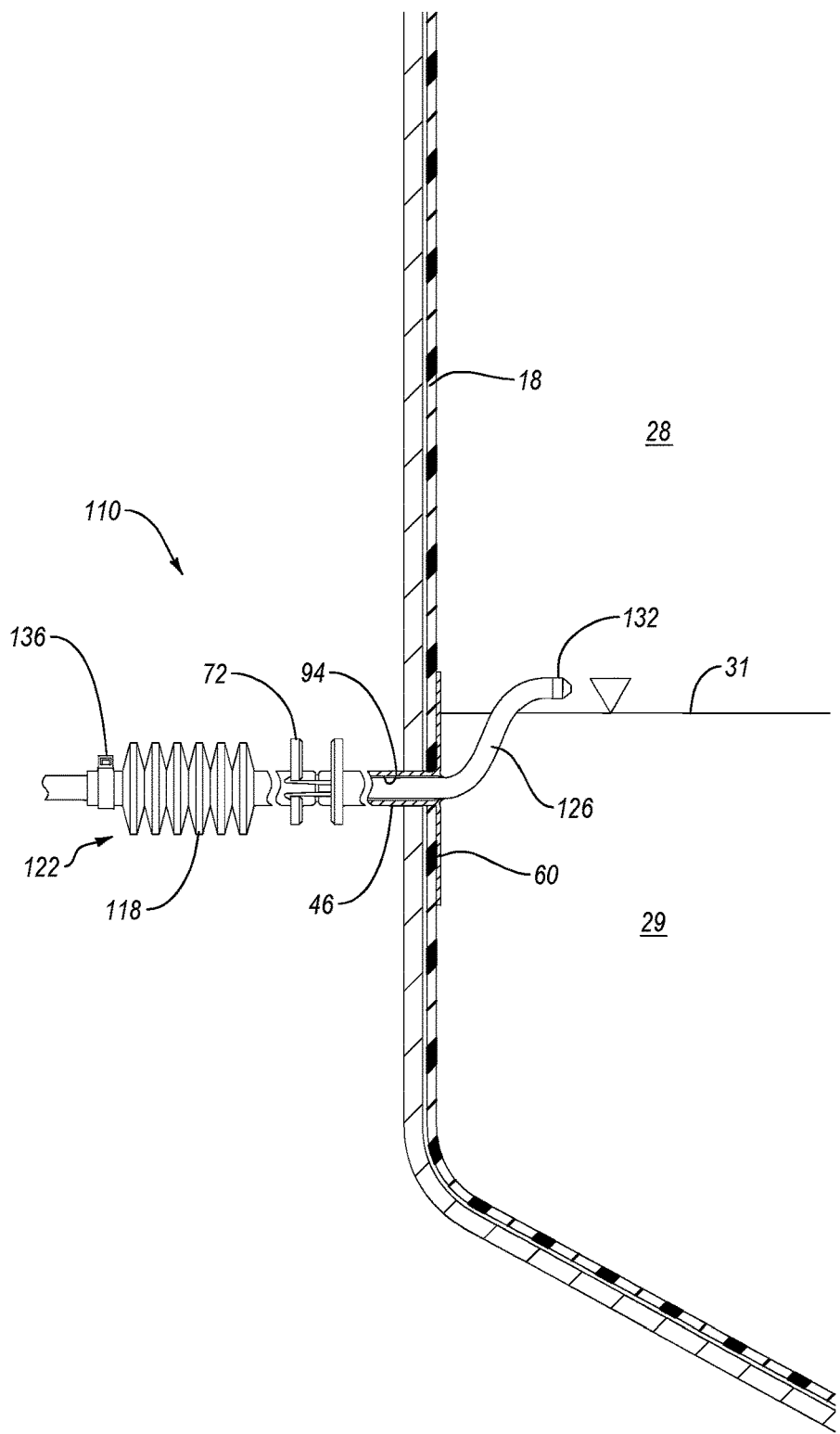
FIG. 5 is a partial cross sectional side view of the gas delivery system shown in FIG. 4 in a second position.

As depicted in FIG. 5, as top surface 31 of culture 29 rises within container 18 to a location at or above passageway 94 of port 46, tube 126 can be advanced further into container 28 by advancing second end 122 of sleeve 118. As a result of the resilient arch of tube 126, tube 126 naturally curves upward within chamber 28 so that nozzle 132 can remain positioned above top surface 31 of culture 29 for blowing gas across top surface 31. As such, delivery system 110 can operate to produce gas stream oxygenation over a range of different elevational levels of top surface 31, i.e., from below passageway 94 to above passageway 94. The distances, dimensions, velocities, flow rates, orientations and the like discussed above with regard to gas delivery system 60A and passageway 66 are also applicable to gas delivery system 110 and outlet 134.

Figure 6:
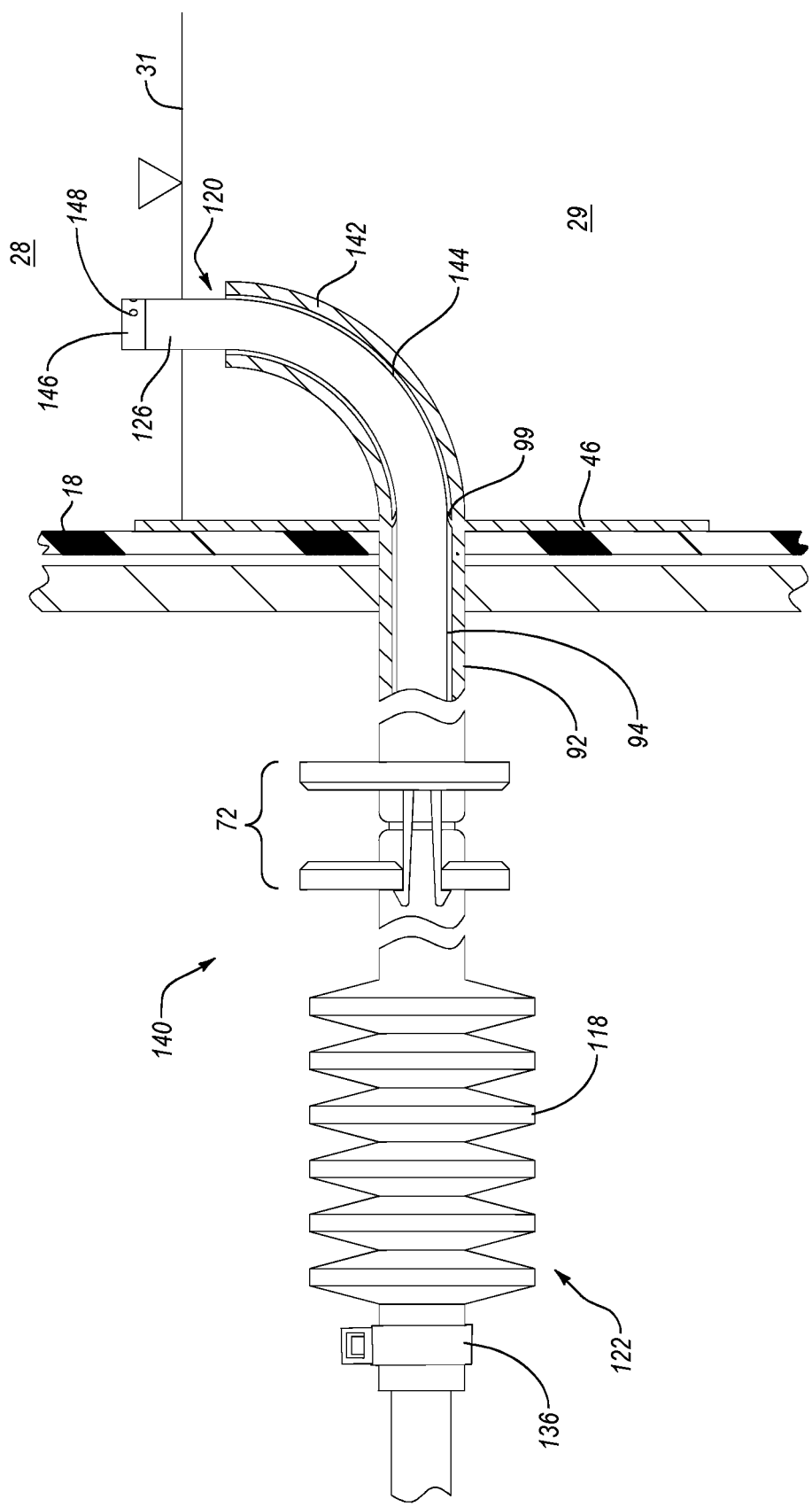
FIG. 6 is a partial cross sectional side view of an alternative embodiment of the gas delivery system shown in FIG. 4.

Depicted in FIG. 6, is yet another alternative embodiment of a gas delivery system 140. Like elements between gas delivery systems 110 and 140 are identified by like characters. Gas delivery systems 110 and 140 are substantially the same except that in system 140 an upwardly curved directing stem 142 is coupled with stem 92 of port 46. Directing stem 142 can be integrally formed with port 46 or can be separately attached thereto by having a portion of directing stem 142 be received within and clamped onto stem 92. Directing stem 142 has a passageway 144 extending therethrough that communicate with passageway 94. In this configuration, as sleeve 118 is collapsed, first end 120 of tube 126 advances through port 46 and into passageway 144 of directing stem 142. As a result of the curvature of directing stem 142, first end 120 is then curved upwards where it exists into compartment 28. As a result of the curvature of directing stem 142, tube 126 need not have a resilient curvature but can comprise a standard flexible tube.

Tube 126 has a nozzle 146 mounted on the end thereof. Formed on the side of nozzle 146 are a plurality of radially spaced apart outlets 148 through which the gas stream outwardly flows. By adjusting the vertical position of nozzle 146, delivery system 140 can again operate over a range of elevations of top surface 31 of culture 29.

FIG. 7 depicts another alternative embodiment of a gas delivery system 163 for delivering a gas stream over top surface 31 of culture 29 for achieving gas stream oxygenation/mass transfer. Gas delivery system 163 can be used independent of or in combination with the other gas delivery systems discussed herein. Gas delivery system 163 comprises a tubular sleeve 162 having a first end 164 and an opposing second end 166. Sleeve 162 has an interior surface 168 that bounds a passageway 170 extending along the length thereof. Sleeve 162 is collapsible and can be made of the same materials and have the same alternative configurations and properties as previously discussed with regard to sleeve 118 (FIG. 6).

Secured to upper end wall 33 of container 18 is a tubular port 171 having a tubular stem 172 projecting therefrom into compartment 28. Second end 166 of sleeve 162 is coupled in sealed engagement to tubular stem 172. Mounted on first end 164 of sleeve 162 is a nozzle 174. Nozzle 174 comprises a body 176 having a first end face 178 and an opposing second end face 180 and an encircling sidewall 182 extending therebetween. A plurality of outlets 184 are formed on sidewall 182 at radially spaced apart locations around sidewall 182. Outlets 184 can also be formed on first end face 178. Outwardly projecting from second end face 184 of nozzle 174 is a tubular stem 186 coupled in sealed engagement with first end 164 of sleeve 162.

Gas delivery system 163 further comprises a tube 189 having a first end that extends down through passageway 170 of sleeve 162 and fluid couples with nozzle 174 and an opposing second end that is disposed outside of container 18 and couples with a gas supply 82A. Although tube 189 can comprise a single continuous tube, in the depicted embodiment tube 189 comprises a first tube portion 190 and a second tube portion 196. First tube portion 190 is disposed within passageway 170 of sleeve 162 and has a first end that is fluid coupled with nozzle 174 so that gas traveling down through first tube portion 190 passes out through outlets 184. A first connector portion 192 is disposed at an opposing second end of first tube portion 190. A gas filter 84 is disposed along first tube portion 190 so that the gas passing therethrough is sterilized.

Second tube portion 196 has a first end with a second connector portion 193 mounted thereon. Connector portions 192 and 193 can be selectively coupled together to form a fluid tight connection therebetween. Connector portions 192 and 193 typically form a sterile connector such as previously discussed connector 72 (FIG. 2). Second tube portion 196 passes out of sleeve 162 and container 18 by passing through tubular port 172. An opposing second end of second tube portion 196 is coupled with gas supply 82A. Thus, in the assembled configuration, gas from gas supply 82A can travel through second tube portion 196, first tube portion 190, and out through outlets 184 of nozzle 174 so as to flow over top surface 31 of culture 29.

Second tube portion 196 can be coiled around a spool. As top surface 31 of culture 29 rises within container 18, the spool can be rotated so that more of tube 189 is wound around the spool. In so doing, nozzle 174 is lifted so that outlets 184 are always maintained at a desired elevation above top surface 31. As nozzle 174 is lifted, sleeve 162 simply collapses or compresses. In contrast, as top surface 31 lowers, tube 189 is unwound from the spool causing nozzle 174 to lower and sleeve 162 to expand. The distances, dimensions, velocities, flow rates, orientations and the like discussed above with regard to the other nozzle outlets are also applicable to outlets 184. It is likewise appreciated that a spool is not required for tube 189 and that any type of lift can be used to raise and lower tube 189. In yet another embodiment, a line, such as a rope or cable, can be passed down sleeve 162 and coupled with nozzle 174 for raising and lowering nozzle 174 so that no undue stress is applied on tube 189 and connector 192/193. Sensors can be used to detect the height of top surface 31 and automatically adjust the height of nozzle 174 accordingly.

In another embodiment, nozzle 174 can be configured to float. This can be accomplished by making nozzle 174 out of a buoyant material or by securing a float to nozzle 174. As a result, nozzle 174 can rest directly on top surface 31 of culture 29 and then automatically raise and lower as top surface 31 raises and lowers. A spool or other lift can still be used for gathering and releasing tube 189.

Gas delivery system 163 is configured so that first tube portion 190, sleeve 162 and nozzle 174 can be preassembled with and sterilized concurrently with container 18. During use, first connector portion 192 can be slid out of sleeve 162 through port 171 and connected with second connector portion 193. After use, connector portions 192/193 can be disconnected and the container assembly disposed of.

Gas delivery system 163 achieves the same function of producing gas stream oxygenation/mass transfer with culture 29 as the previously discussed gas delivery systems. However, gas delivery system 163 has the further advantage that nozzle 174 can be more centrally located on or above top surface 31 and can dispense gas radially outwardly so as to more uniformly apply the gas over all or most of the area of top surface 31. Furthermore, the mass transfer can be more constantly maintained because outlets 184 can be continuously maintained at a desired elevation above top surface 31.

Figure 8:
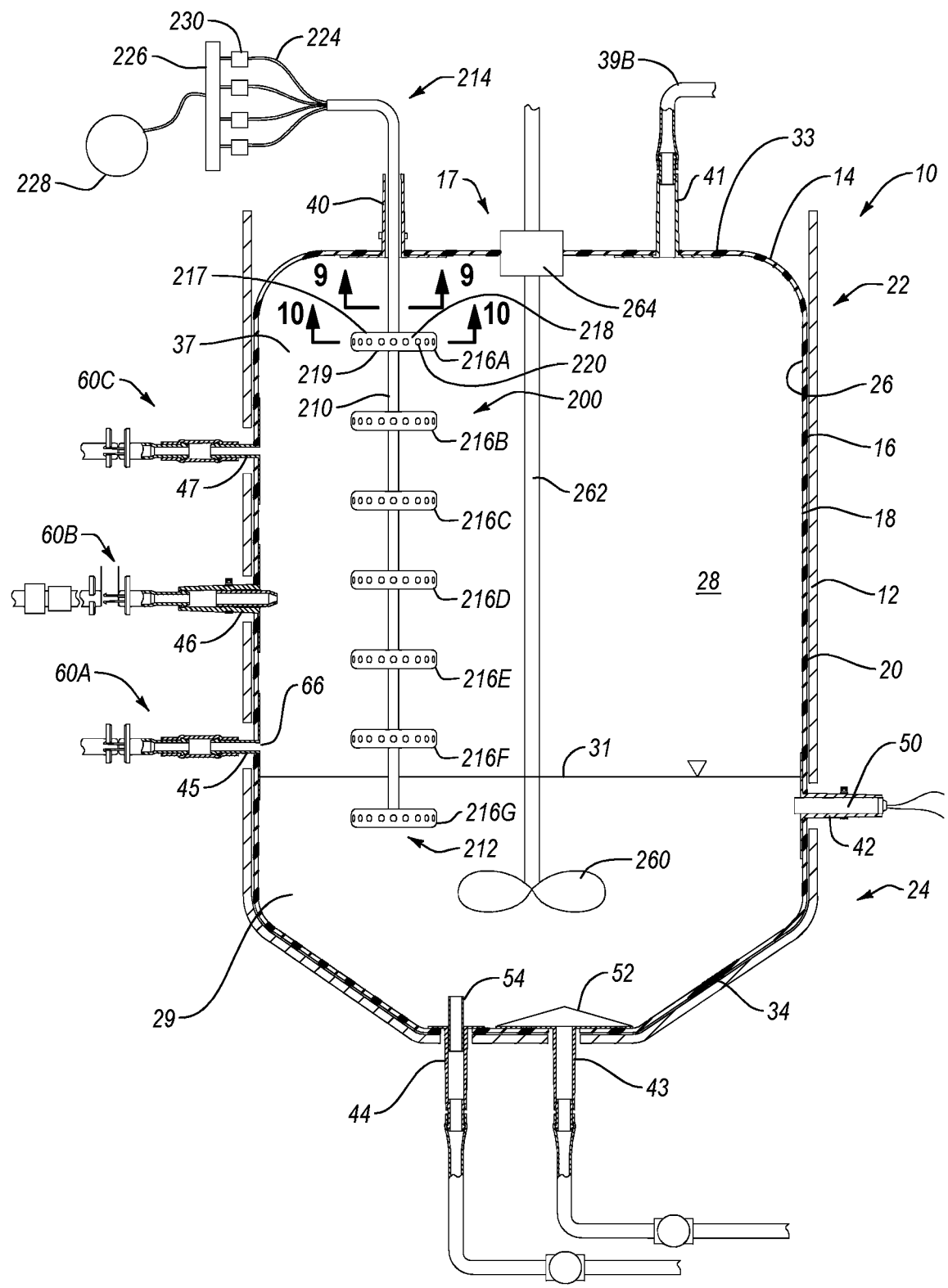
FIG. 8 is a cross sectional side view of the reactor system shown in FIG. 1 that includes a further alternative embodiment of a gas delivery system comprising a multi-lumen tube having a plurality of spaced apart nozzles connected thereto.
Figure 9:
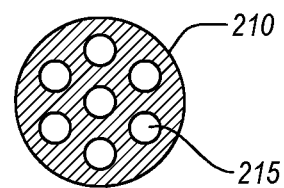
FIG. 9 is a cross sectional side view of the tube shown in FIG. 8 taken along section lines 9-9 in FIG. 8.

Depicted in FIG. 8 is yet another alternative embodiment of a gas delivery system 200 that incorporates features of the present invention and can achieve gas stream oxygenation/mass transfer with culture 29. Gas delivery system 200 can also be used in conjunction with or independent of the other gas delivery systems disclosed herein. Gas delivery system 200 comprises a tube 210 having a first end 212 and an opposing second end 214. As depicted in FIG. 9, tube 210 has a plurality of lumens 215 extending along at least a portion of the length of tube 210. A plurality of nozzles 216A-G are coupled with tube 210 at spaced apart location along the length thereof. Each nozzle 216 encircles and radially outwardly projects from tube 210. Each nozzle 216 has a top surface 217, an opposing bottom surface 219 and an encircling side surface 218 extending therebetween. A plurality of outlets 220 are formed of side surface 218 at radially spaced apart locations around nozzle 216. Outlets 220 can also be formed on bottom surface 219. The distances, dimensions, velocities, flow rates, orientations and the like discussed above with regard to the other nozzle outlets are also applicable to outlets 220.

Figure 10:
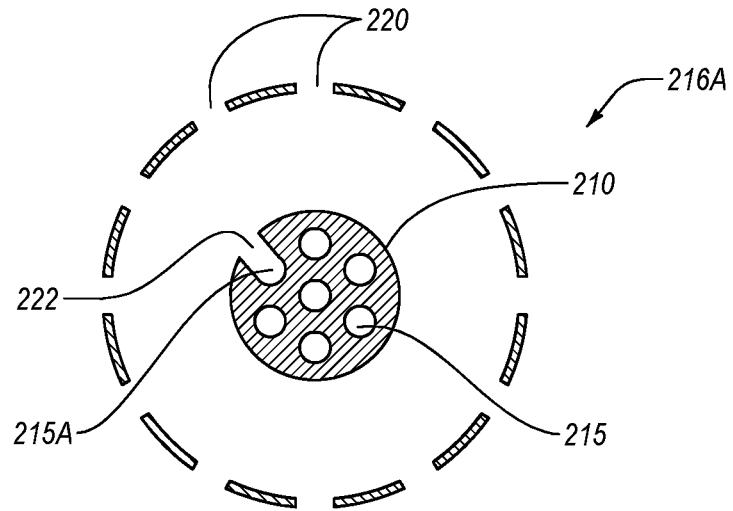
FIG. 10 is a cross sectional side view of the nozzle shown in FIG. 8 taken along section lines 10-10 in FIG. 8.

Each lumen 215 of tube 210 has an opening that communicates with a corresponding nozzle 216A-G. For example, as depicted in FIG. 10, within nozzle 216A an opening 222 is formed on tube 210 so as to communicate with a lumen 215A. As such, gas traveling down through lumen 215A passes out of opening 222 and into nozzle 216A. The gas radially passes out of nozzle 216A through outlets 220 so that it can pass over top surface 31 of culture 29. Each nozzle 216B-G is similarly configured with a corresponding opening 222 communicating with a separate lumen 215 therein.

Returning to FIG. 8, second end 214 of tube 210 passes in sealed connection through port 40 so as to be disposed outside of container 18. A separate secondary tube 224 is fluid coupled with each lumen 215. The opposing end of each secondary tube 224 is fluid coupled with a manifold 226 which in turn is fluid coupled to a gas supply 228. A separate valve 230 is disposed along each secondary tube 224 and is controlled by a central controller. Accordingly, as culture 29 raises and lowers within container 18, the controller selectively opens or closes valves 230 so that only the nozzle 216 that is directly above top surface 31 has gas flowing therethrough. For example, in FIG. 8, only the valve 230 coupled to the secondary tube 224 that feeds gas to nozzle 216F would be opened. The remaining valves 230 would be closed. For nozzles 216 that are below top surface 31 and thus within culture 29, it is appreciated that corresponding valves 230 can be slightly opened so that a positive gas pressure is produced within the submerged nozzle 216 and thereby preclude fluid from entering therein. If desired, a positive pressure can also be applied to the other nozzles 216 that are not in use.

As top surface 31 of culture 29 raises to nozzle 216F, gas would be closed off to nozzle 216F and opened to nozzle 216E. Again, gas passing out through nozzles 216 flows over top surface 31 so as to produce a gas stream oxygenation/mass transfer therewith. As with gas delivery system 163, gas delivery system 200 has the advantage that nozzles 216 can be more centrally located on or above top surface 31 and can dispense gas radially outwardly so as to more uniformly apply the gas over all or most of the area of top surface 31. Furthermore, multiple nozzles 216 can be easily placed at adjacent locations along tube 210 so that the gas stream is more uniformly maintained on top surface 31, thereby more consistently maintaining the mass transfer.

In addition to the above, it is appreciated that there are other gas delivery systems that can be used to deliver a gas stream into container 28 to achieve gas stream oxygenation/mass transfer. In addition, it is appreciated that the gas need not be delivered through side 20 of container 20. For example, by adjusting the size of the passageway extending through access port 40 (shown in FIG. 1) or by positioning nozzle 96 (shown in FIG. 3) therein, a gas flow could be passed therethrough at a sufficient flow rate and speed so that the gas will travel downwardly from port 40 to the top surface 31 and then will be deflected to travel horizontally or substantially horizontally across top surface 31 so as to produce gas stream oxygenation of culture 29. In other embodiments, gas delivery system 140 shown in FIG. 6, minus directing stem 142, could be mounted on upper end wall 33 (shown in FIG. 1). In this embodiment, tube 126 could be lowered within compartment 28 until nozzle 146 is located a proper distance above top surface 31 to produce gas stream oxygenation/mass transfer. In turn, as the level of culture 29 increases within compartment 28, tube 126 and nozzle 146 can be drawn upward so that nozzle 146 remains at the optimal position for gas stream oxygenation/mass transfer. This embodiment is similar to gas delivery system 163.

Returning to FIG. 1, reactor system 10 also includes mixing system 17 which is used to mix culture 29 so that it remains substantially homogeneous and is uniformly oxygenated. In the depicted embodiment, mixing system comprises a drive shaft 262 that projects into container 18 and an impeller 260 mounted on drive shaft 262 so that as drive shaft 262 rotates, impeller 260 rotates within culture 29. A dynamic seal 264 forms an aseptic seal between drive shaft 262 and container 18 while still enabling rotation of drive shaft 262. In some embodiments, the term "impeller" can refer to any device that is used for agitating or mixing the contents of a stirred-tank reactor system (e.g., bioreactor). The impeller may agitate the fluidic medium by stirring or other mechanical motion. Examples of impellers that can be used in the present instant invention include, but are not limited to, a Rushton, a marine, a hydrofoil, a pitched blade, and any other commercially available impeller.

It is appreciated that a variety of other mixing systems can also be incorporated into reactor system 10. For example, in contrast to drive shaft 162 rotating impeller 160, a drive shaft can be used that vertically raises and lowers an impeller or mixing element for mixing the culture. In yet other embodiments, the drive shaft can be eliminated and impeller 160 can be magnetically driven. In still other embodiments, the drive shaft and impeller can be eliminated and mixing can be accomplished by rocking container 18 so that the culture is mixed therein. In this embodiment, container 18 can be placed on a rocker table rather than being disposed within support housing 12. A pulsating disk, paddle mixer, or sill other mixing elements can also be used for mixing the culture. Other embodiments for driving an impeller within a reactor are disclosed in US Publication No. 2013/0101982, published Apr. 25, 2013, which is incorporated herein by specific reference in its entirety. The above examples for mixing culture 29 are examples of means for mixing culture 29 or other fluid that may be contained within container 12.

The above methods and systems have primarily been discussed in association with oxygenating a culture within a reactor. As previously mentioned, however, that the same methods and systems for passing a gas stream over a fluid surface to achieve gas stream mass transfer can also be used for other purposes. For example, the inventive methods and systems can be used for entraining oxygen or other types of gases into fluids other than a culture. In other embodiments, in contrast to oxygenating through a gas stream that passes over the top surface of the culture, oxygenation in a reactor could be accomplished by conventional mechanisms through a sparger, such as sparger 52. The inventive system could then be used to deliver a stream of pure nitrogen over the surface of the culture. The nitrogen would be transferred into the culture and used to strip $CO_2$ from the culture. The same process can also be used for stripping other gases from other types of fluids. Thus, the inventive gas stream mass transfer can be used for both entraining a gas into a fluid and stripping a gas from a fluid. The circulation produced by the nitrogen stream or other inert gasses could also entrain oxygen introduced through inlet port 40 to supplement oxygen provided by the sparger.

In another example, when it is desired to operate an anaerobic system, nitrogen or other inert gasses could be passed over the surface of the culture so as to purge out oxygen from the culture. Accordingly, the inventive methods and systems disclosed herein can be used in any biological, chemical, food or other processing or production where it is desired to affect a mass transfer of any gas into or out of a liquid.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for performing a gas-liquid mass transfer, the method comprising:

(a) mixing a liquid within a compartment of a container, the liquid having an exposed top surface disposed within the compartment of the container;

(b) moving a tube within the container so that an outlet on the tube or on a nozzle connected to the tube is positioned within a head space at a location above the top surface of the liquid; and (c) blowing a stream of gas into the head space through the outlet so that the stream of gas is blown over at least a portion of the top surface of the liquid while the liquid is being mixed within the container so as to produce a gas-liquid mass transfer between the gas and the liquid.

2. The method as recited in claim 1, wherein the liquid comprises a biological suspension comprised of cells or microorganisms suspended within a growth medium.

3. The method as recited in claim 1, wherein the container comprises a flexible bag having a bottom wall, a top wall and an encircling sidewall extending therebetween, the step of blowing the stream of gas comprising delivering the gas through a first opening formed on the container.

4. The method as recited in claim 1, wherein the step of blowing the stream of gas comprises delivering the gas through the nozzle coupled to or disposed within the compartment of the container.

5. The method as recited in claim 1, wherein the stream of gas produces a kLa factor in the liquid of at least 3.

6. The method as recited in claim 1, wherein the step of moving the tube comprises:
   advancing the tube through a first opening formed on the container so that a first end of the tube is located within the compartment of the container.

7. The method as recited in claim 1, wherein the step of blowing the stream of gas over the at least a portion of top surface of the liquid occurs without sparging a gas into the liquid.

8. The method as recited in claim 1, wherein the top surface of the liquid is at a first elevation within the container during the step of blowing the stream of gas, the step of blowing the stream of gas over the at least a portion of the top surface of the liquid occurring without sparging a gas into the liquid while the liquid is at the first elevation, and the method further comprising:
   a) adding a growth medium to the liquid within the container so as to raise the top surface of the liquid to a second elevation within the compartment; and
   b) sparging a gas into the liquid after the top surface has been raised to the second elevation within the compartment.

9. The method as recited in claim 1, wherein the step of mixing the liquid comprises rotating a mixing element within the compartment of the container.

10. The method as recited in claim 1, wherein the step of mixing is performed independent of blowing the stream of gas.

11. The method as recited in claim 1, wherein the step of moving the tube comprises moving at least a portion of the tube vertically within the compartment of the container.

12. A method for performing a gas-liquid mass transfer, the method comprising:
   (a) mixing a liquid within a compartment of a container, the liquid having an exposed top surface disposed within the compartment of the container;
   (b) advancing a tube within a first opening formed on the container so that a first end of the tube is positioned at a desired location above the top surface of the liquid within the compartment of the container; and
   (c) blowing a stream of gas out the first end of the tube so that the stream of gas passes over at least a portion of the top surface of the liquid while the liquid is being mixed within the container so as to produce a gas-liquid mass transfer between the gas and the liquid.

13. The method as recited in claim 12, wherein the step of blowing the stream of gas over the at least a portion of top surface of the liquid occurs without sparging a gas into the liquid.

14. The method as recited in claim 12, wherein the step of mixing the liquid comprises rotating a mixing element within the compartment of the container.

15. The method as recited in claim 12, wherein the liquid comprises a biological suspension comprised of cells or microorganisms suspended within a growth medium.

16. The method as recited in claim 12, wherein the step of advancing the tube comprises moving at least a portion of the tube vertically within the compartment of the container.

17. A method for performing a gas-liquid mass transfer, the method comprising:
   (a) mixing a liquid within a compartment of a container, the liquid having an exposed top surface disposed within the compartment of the container;
   (b) blowing a stream of gas over at least a portion of the top surface of the liquid while the liquid is being mixed within the container so as to produce a gas-liquid mass transfer between the gas and the liquid, wherein the top surface of the liquid is at a first elevation within the container during the step of blowing the stream of gas, the step of blowing the stream of gas over the at least a portion of the top surface of the liquid occurring without sparging a gas into the liquid while the liquid is at the first elevation;
   (c) adding a further liquid to the liquid within the container so as to raise the top surface of the liquid to a second elevation within the compartment; and
   (d) sparging a gas into the liquid within the container after the top surface has been raised to the second elevation within the compartment.

18. The method as recited in claim 17, wherein the liquid comprises a biological suspension comprised of cells or microorganisms suspended within a growth medium.

19. The method as recited in claim 17, wherein the container comprises a flexible bag.

20. The method as recited in claim 17, wherein the step of mixing the liquid comprises rotating a mixing element within the compartment of the container.

* * * * *